(12) United States Patent
Altman et al.

(10) Patent No.: US 7,104,988 B2
(45) Date of Patent: *Sep. 12, 2006

(54) CARDIAC DRUG DELIVERY SYSTEM

(75) Inventors: Peter A. Altman, San Francisco, CA (US); John D. Altman, Palo Alto, CA (US)

(73) Assignee: Biocardia, Inc., South San Francisco, CA (US)

( * ) Notice: Subject to any disclaimer, the term of this patent is extended or adjusted under 35 U.S.C. 154(b) by 457 days.

This patent is subject to a terminal disclaimer.

(21) Appl. No.: 10/101,301

(22) Filed: Mar. 19, 2002

(65) Prior Publication Data

US 2002/0156383 A1  Oct. 24, 2002

Related U.S. Application Data

(62) Division of application No. 09/260,641, filed on Mar. 2, 1999, now Pat. No. 6,358,247, which is a division of application No. 08/816,850, filed on Mar. 13, 1997, now Pat. No. 6,086,582.

(51) Int. Cl.
*A61N 1/05* (2006.01)

(52) U.S. Cl. ............................ 606/41; 607/3; 607/120

(58) Field of Classification Search ......... 600/374–375, 600/508; 606/47, 41, 43, 48, 44; 607/3, 120–122, 607/126–128, 60–61, 32–33; 604/264, 21
See application file for complete search history.

(56) References Cited

U.S. PATENT DOCUMENTS

| | | | | | |
|---|---|---|---|---|---|
| 6,086,582 | A | * | 7/2000 | Altman et al. | 606/41 |
| RE37,463 | E | * | 12/2001 | Altman | 600/374 |
| 6,358,247 | B1 | * | 3/2002 | Altman et al. | 606/41 |

* cited by examiner

*Primary Examiner*—Eleni Mantis Mercader
(74) *Attorney, Agent, or Firm*—Larkin Hoffman Daly & Lindgen Ltd.; Frederick W. Niebuhr, Esq

(57) ABSTRACT

A system is disclosed, for administering a therapeutic agent locally and to a depth within cardiac tissue. An elongate, flexible catheter contains a flexible electric conductor and supports at its distal end an implantable electrode incorporating a penetrating element, typically a fixation helix or a linear needle that penetrates cardiac tissue as the electrode is implanted. A therapeutic agent is delivered through the electrode, to the cardiac tissue surrounding the penetrating element. The electrode can act as a sensor, to monitor an electrical condition of the surrounding cardiac tissue, and to control delivery of the agent responsive to the sensed electrical condition. Several embodiments feature a distal reservoir adjacent the electrode for effecting transient deliveries of the therapeutic agent in minute quantities. Other embodiments are disclosed for providing sustained deliveries of the agents.

36 Claims, 12 Drawing Sheets

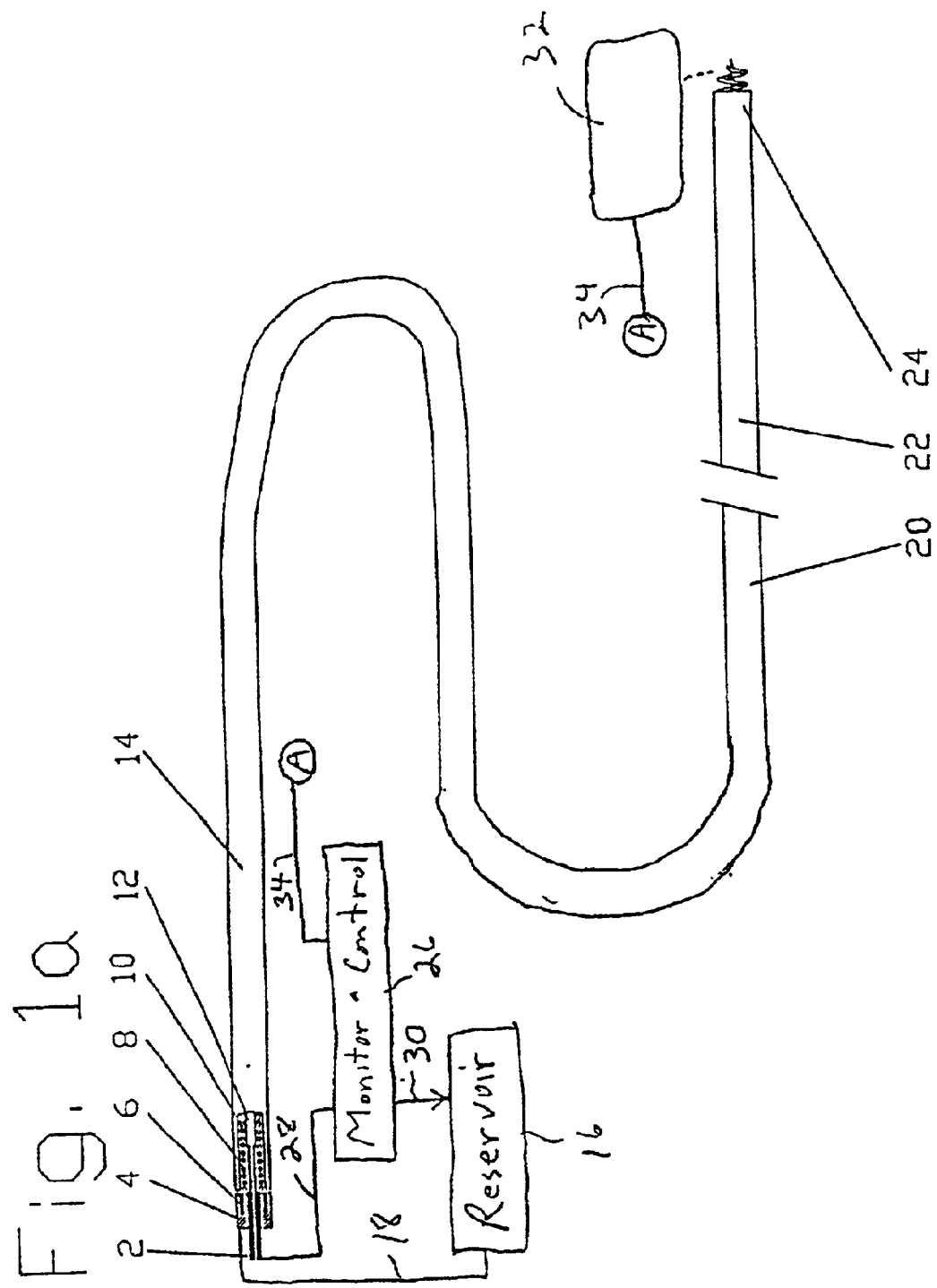

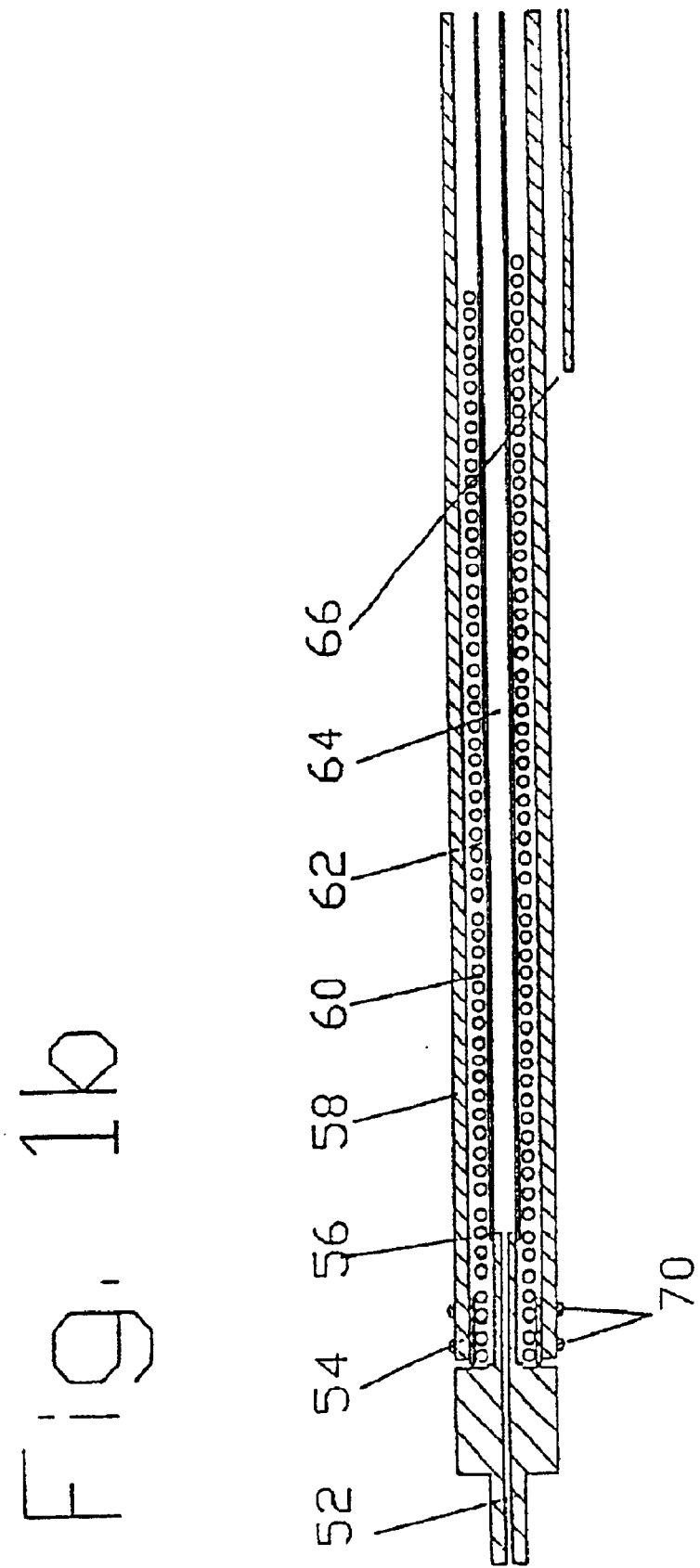

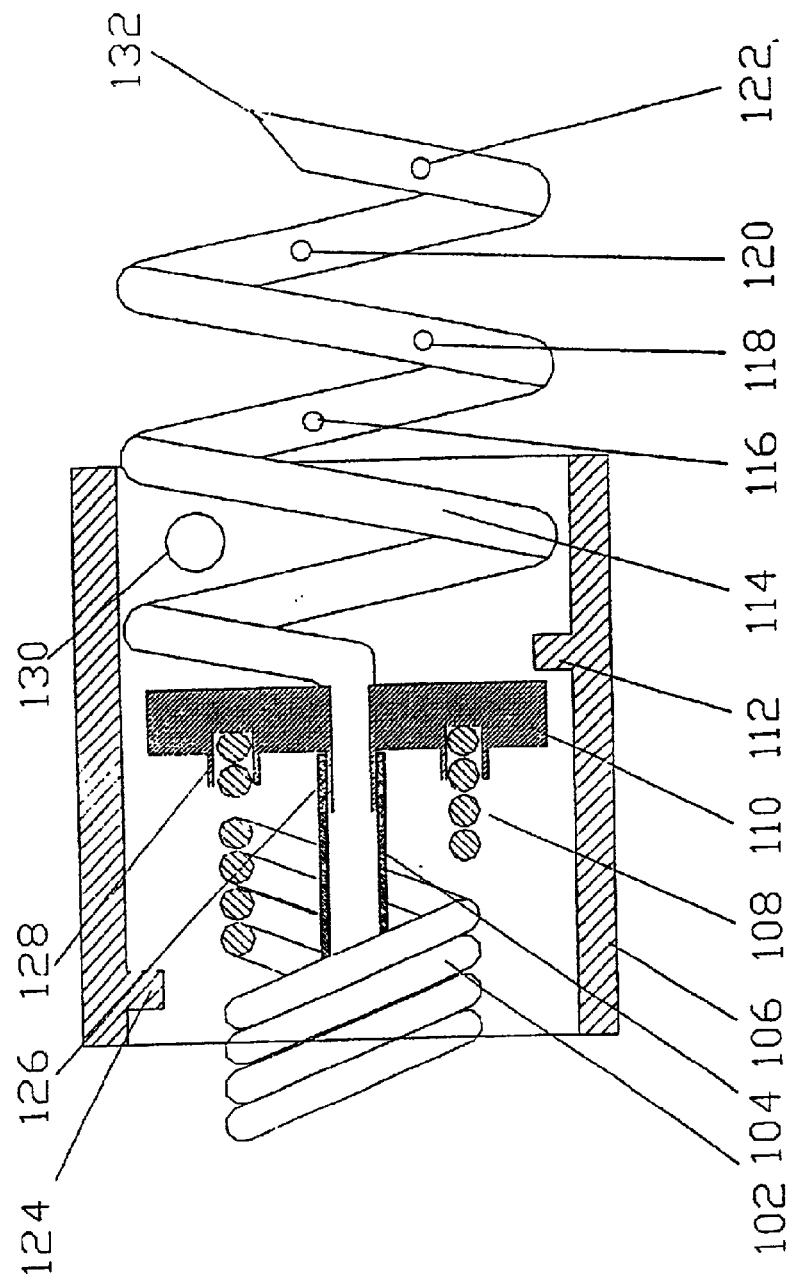

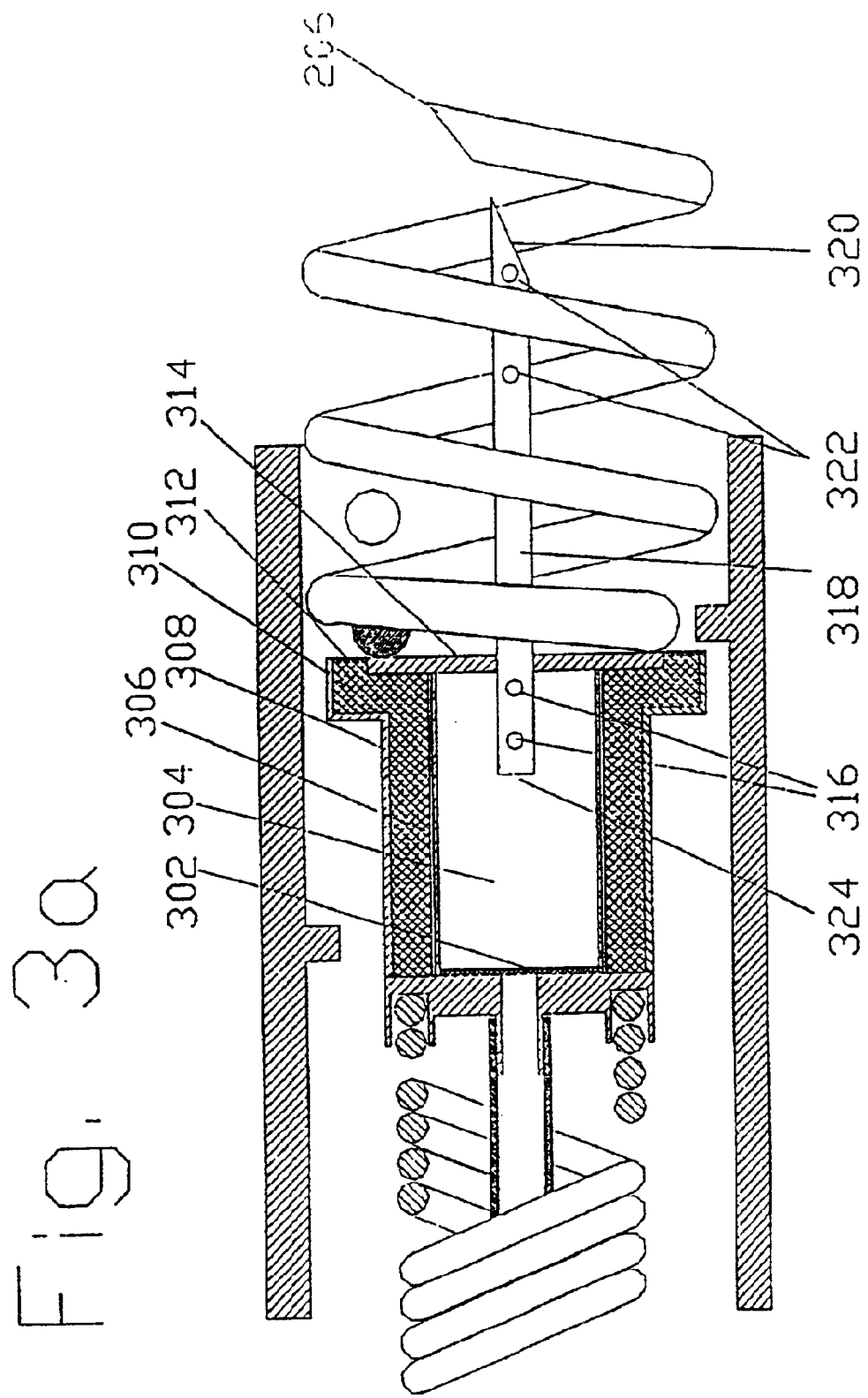

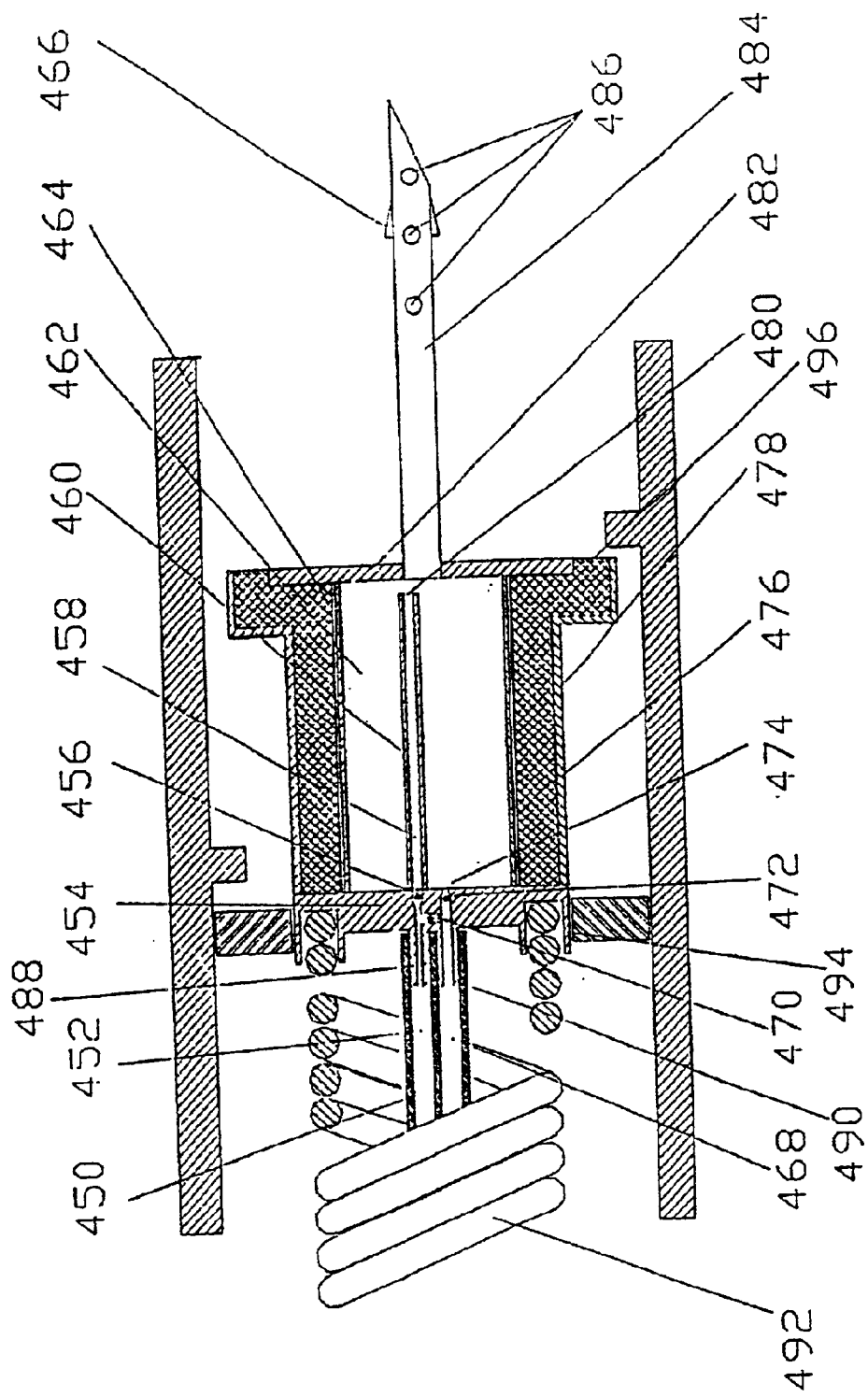

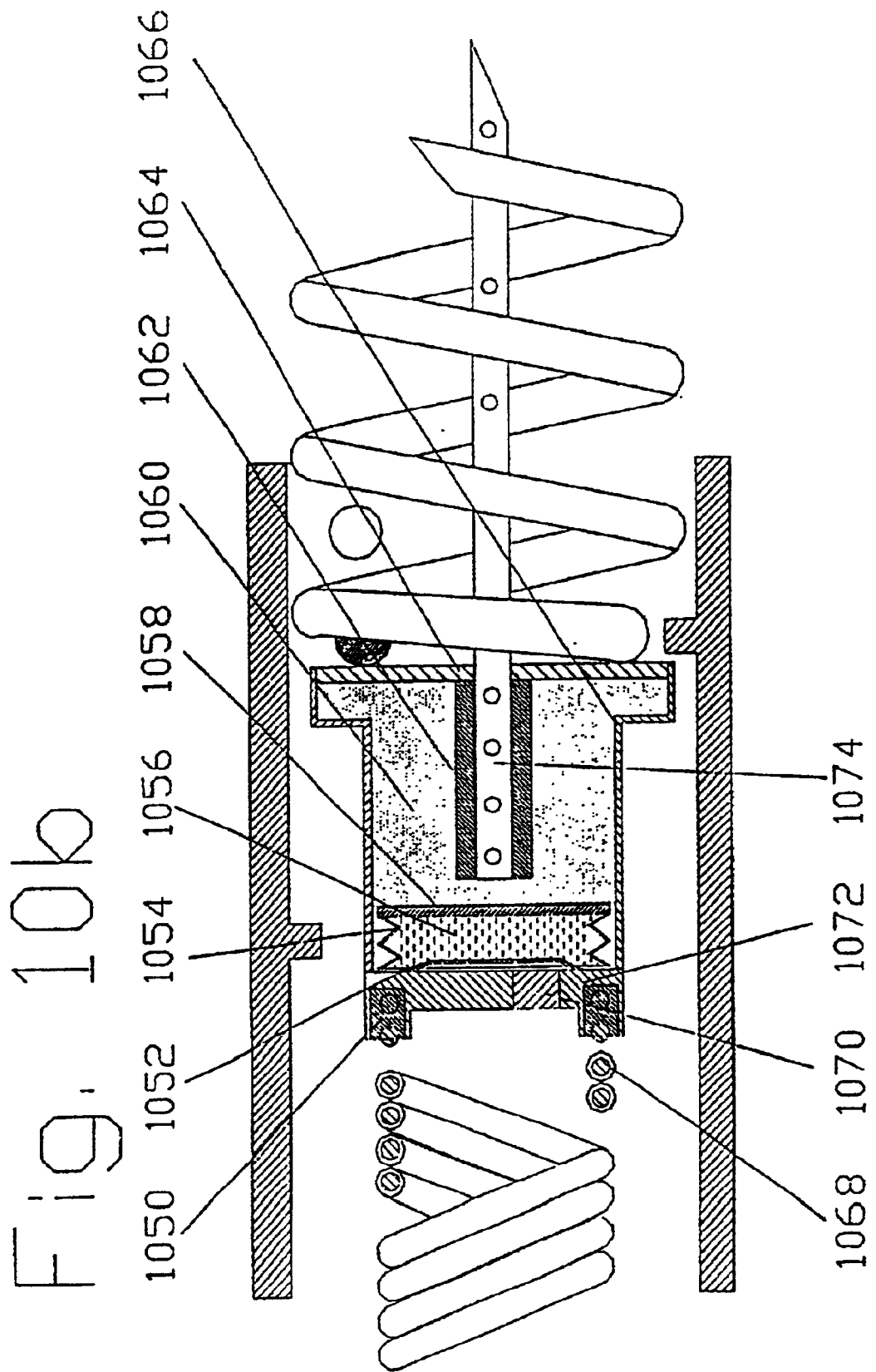

CARDIAC DRUG DELIVERY SYSTEM

This is a divisional of prior application Ser. No. 09/260,641 (now U.S. Pat. No. 6,358,247), filed Mar. 2, 1999 as a divisional of application Ser. No. 08/816,850 (now U.S. Pat. No. 6,086,582), filed Mar. 13, 1997.

FIELD OF THE INVENTION

This invention relates to site specific delivery of therapeutic agents, structures and catheter systems to achieve site specific delivery of therapeutic agents, and means for implanting and using these systems to enable delivery of therapeutic agents to the body. More specifically, this invention relates to delivery of pharmacological agents to specific regions of the heart at a depth within the heart wall.

BACKGROUND OF THE INVENTION

It is possible to identify particular sites within the myocardium which may benefit from local drug release therapy. Examples of problematic tissue which may benefit form local drug release therapy are ischemic sites and arrhythmogenic sites. Different means and methods for delivering agents to these sites will be disclosed in detail.

Ischemic Sites

Ischemic tissue is characterized by limited metabolic processes which cause poor functionality. The tissue lacks oxygen, nutrients, and means for disposing of wastes. This hinders the normal functioning of the heart cells or myocytes in an ischemic region. If an ischemic, or damaged, region of the heart does not receive enough nutrients to sustain the myocytes they are said to die, and the tissue is said to become infarcted. Ischemia is reversible, such that cells may return to normal function once they receive the proper nutrients. Infarction is irreversible.

Non-invasive systemic delivery of anti-ischemic agents such as nitrates or vasodilators allows the heart to work less by reducing vascular resistance. Some vascular obstructions are treated by the systemic delivery of pharmacological agents such as TPA, urokinase, or antithrombolytics which can break up the obstruction. Catheter based techniques to remove the vascular obstructions such as percutaneous transluminal coronary angioplasty (PTCA), atherectomy devices, and stents can increase myocardial perfusion. More drastic, but very reliable procedures such as coronary artery bypass surgery can also be performed. All of these techniques treat the root cause of poor perfusion.

It should be noted that these therapies are primarily for the treatment of large vessel disease, and that many patients suffer from poor perfusion within smaller vessels that cannot be treated with conventional therapies.

The delivery of angiogenic growth factors to the heart via the coronary arteries by catheter techniques, or by implantable controlled release matrices, can create new capillary vascular growth within the myocardium. Recent work has shown substantial increases in muscular flow in a variety of in vivo experimental models with growth factors such as Tumor Angiogenic factor (TAF), basic fibroblast growth factor (bFGF), vascular endothelial growth factor (VEGF), and acidic fibroblast growth factor (aFGF). The methods of delivering these agents to the heart include implantable controlled release matrices such as ethylene vinyl acetate copolymer (EVAC), and sequential bolus delivery into the coronary arteries. Recently similar techniques have been attempted in peripheral vessels in human patients with the primary difficulty being systemic effects of the agents delivered.

U.S. Pat. No. 5,244,460 issued to Unger describes a method of introducing growth factors over time by delivering them through fluid catheters into the coronary arteries, but this does not result in efficient delivery of these agents to the ischemic tissue. If these or other agents are delivered to the coronary artery, a region of tissue that is equivalent to that supplied by the artery will receive the therapeutic agents. This may be substantially more tissue than is in need of local drug delivery therapy. Further, if a vessel is occluded, the growth factors will act in the tissue which the coronary arteries successfully perfuse. As the underlying problem of ischemic tissue is poor perfusion, excess growth factor must be delivered in order to obtain the desired effects in the poorly perfused tissue. Further, growth factors may cause unwanted angiogenesis in tissues where inappropriately delivered. The cornea is described by Unger as such a location, but perhaps more critical is inappropriate delivery of these factors to the brain. Further, placement of delivery devices within these coronary arteries as Unger describes tends to obstruct these arteries and may augment occlusive thrombosis formation. There is a significant need for minimizing the amount of growth factors for introducing angiogenesis by delivering these agents only to the site where they are most needed.

There are complications with clinically acceptable procedures where special devices for delivering agents to ischemic tissue will be useful. After opening vessels using PTCA, the vessels often lose patentcy over time. This loss of patentcy due to re-stenosis may be reduced by appropriate pharmacological therapy in the region of the artery. There is a need for new techniques that will enable pharmacological therapy to reduce the incidence of restenosis.

Arrhythmogenic Sites

Cardiac arrhythmias are abnormal rhythmic contractions of the myocardial muscle, often introduced by electrical abnormalities, or irregularities in the heart tissue, and not necessarily from ischemic tissue. In a cardiac ablation procedure, the arrhythmogenic region is isolated or the inappropriate pathway is disrupted by destroying the cells in the regions of interest. Using catheter techniques to gain venous and arterial access to the chambers of the heart, and possibly trans septal techniques, necrotic regions can be generated by destroying the tissue locally. These necrotic regions effectively introduce electrical barriers to problematic conduction pathways.

U.S. Pat. No. 5,385,148 issued to Lesh describes a cardiac imaging and ablation catheter in which a helical needle may be used to deliver fluid ablative agents, such as ethanol, at a depth within the tissue to achieve ablation. Lesh further describes a method of delivering a pharmacological agent to the tissue just before performing the chemical ablation procedure to temporarily alter the conduction of the tissue prior to performing the ablation. Such temporary alteration of tissue has the advantage of allowing the physician to evaluate the results of destructive ablation in that region prior to actually performing the ablation. This method of ablation has the advantage that the ablative fluid agents are delivered to essentially the same tissue as the temporary modifying agents. However, with ablative fluid agents it is difficult to control the amount of tissue which is destroyed—especially in a beating heart, and ablative RF energy is in common use because of its reproducible lesions and ease of control. There is a need for an ablation catheter that uses a single structure within the heart wall for both temporary modification of tissue conductivity by delivery of therapeutic agents at a depth within the tissue, and delivery of RF energy.

U.S. Pat. No. 5,527,344 issued to Arzbaecher and incorporated by reference herein, describes a pharmacological atrial defibrillator and method for automatically delivering a defibrillating drug into the bloodstream of a patient upon detection of the onset of atrial arrhythmias in order to terminate the atrial arrhythmias. By delivering agents to a blood vessel, Arzbaecher requires systemic effects to be achieved in order to terminate the atrial arrhythmias. The advantages of local drug delivery are absent from the system described. There is a need for a system and method to transiently treat atrial arrhythmias by local delivery of pharmacological agents which affect the excitation of the cardiac tissue locally.

Many patents describe systems for delivering anti inflammatory agents to the endocardial surface of the heart. Such surface delivery is less viable for regions at a depth within the tissue. Further, because of the volume of fluid moving by the inner surfaces of the heart, higher concentrations may be required at the surface to counteract the effects of dilution. These higher doses result in greater likelihood of problematic systemic effects from the therapeutic agents. Delivering agents within the tissue will minimize the dilution of agents, and decrease the possibility of the agents being delivered to inappropriate sites. This is particularly important with growth factors whose systemic affects are not well documented, just as it is important for antiarrhythmic agents whose pro-arrhythmia systemic effects have been recognized. There is a need for a means to deliver agents to ischemic and arrhythmogenic sites within the myocardium.

To deliver substances at a depth within the heart, U.S. Pat. Nos. 5,447,533 and 5,531,780 issued to Vachon describe pacing leads having a stylet introduced anti inflammatory drug delivery dart and needle advanceable from the distal tip of the electrode. U.S. Pat. No. 5,002,067 issued to Berthelson describes a helical fixation device with a groove to provide a path to introduce anti-inflammatory drug to a depth within the tissue. U.S. Pat. No. 5,324,325 issued to Moaddeb describes a myocardial steroid releasing lead whose tip of the rigid helix has an axial bore filled with a therapeutic medication such as a steroid or steroid based drug. None of these patents provides a means for site specific delivery of agents as all applications of the drug delivery systems are at the location selected for pacing. None of these provides a means or method for delivering agents to ischemic or infarcted tissues. Only Vachon and Moaddeb provide a means for effectively delivering the anti-inflammatory agents to a depth within the myocardium. U.S. Pat. No. 5,551,427 issued to Altman describes a catheter system capable of delivering drugs to the heart at a depth within the heart tissue.

U.S. Pat. No. 5,431,649 issued to Mulier describes a hollow helical delivery needle to infuse the heart tissue with a conductive fluid prior to ablation to control the lesion size produced. The system does not have drug delivery capabilities.

None of the prior art includes the use of macromolecular controlled release matrices such as ethylene vinyl acetate copolymer to deliver agents with large molecular weights to a depth within the heart tissue.

OBJECTS AND ADVANTAGES

In general it is an object of the present invention to provide a biocompatible drug delivery catheter which will improve the ability to deliver drugs to a depth within the heart tissue.

Another object of the invention is the delivery of growth factors to a depth within the heart tissue over an extended period of time to increase collateral flow in poorly perfused tissue.

Yet another object of the invention is to provide a permanently implantable system that will enable transient delivery of pharmacological agents to a depth within the heart tissue such that cardiac arrhythmias may be terminated.

It is also an object of the invention to provide a combination drug delivery and ablation catheter that will enable a region of the heart tissue to be modified pharmacologically prior to performing RF ablation at a depth within the heart tissue.

It is a further object of the invention to provide catheters with implantable osmotic pumps at their distal ends that deliver pharmacological agents to a depth within the myocardium.

Another object of the invention is to provide catheters with controlled release matrices at their distal ends that deliver pharmacological agents to a depth within the heart tissue.

A further object of the invention is to provide catheters with fluid pathways from proximally located reservoirs which may deliver fluids to a depth within the myocardium, with an electrical conductor to sense the heart so an external device may determine when to deliver pharmacological therapy to a depth within the heart tissue.

A further object of the invention is to provide catheters with fluid pathways from proximally located reservoirs which may deliver fluids to a depth within the myocardium, with a high conductivity electrical conductor capable of delivering RF therapy to the heart from the metallic structure used to deliver drugs to the heart.

Yet another object of the invention is to provide catheters with a means to clear the agents from a catheter and replace them with other agents.

Further objects and advantages of this invention will become apparent from a consideration of the drawings and ensuing description.

DESCRIPTION OF THE DRAWINGS

FIG. 1a is a partial cross sectional view of a drug delivery catheter.

FIG. 1b is a cross sectional view of the proximal portion of a dual lumen drug delivery catheter.

FIG. 1c is a partial cross sectional view of the distal portion of a drug delivery catheter with a hollow fixation helix.

FIG. 4 is a partial sectional view of a distal portion of a drug delivery catheter.

FIG. 10b is a partial cross sectional view of the distal portion of drug delivery catheter with a vapor pressure transient delivery means.

DETAILED DESCRIPTION OF THE PREFERRED EMBODIMENTS

Figure 2:
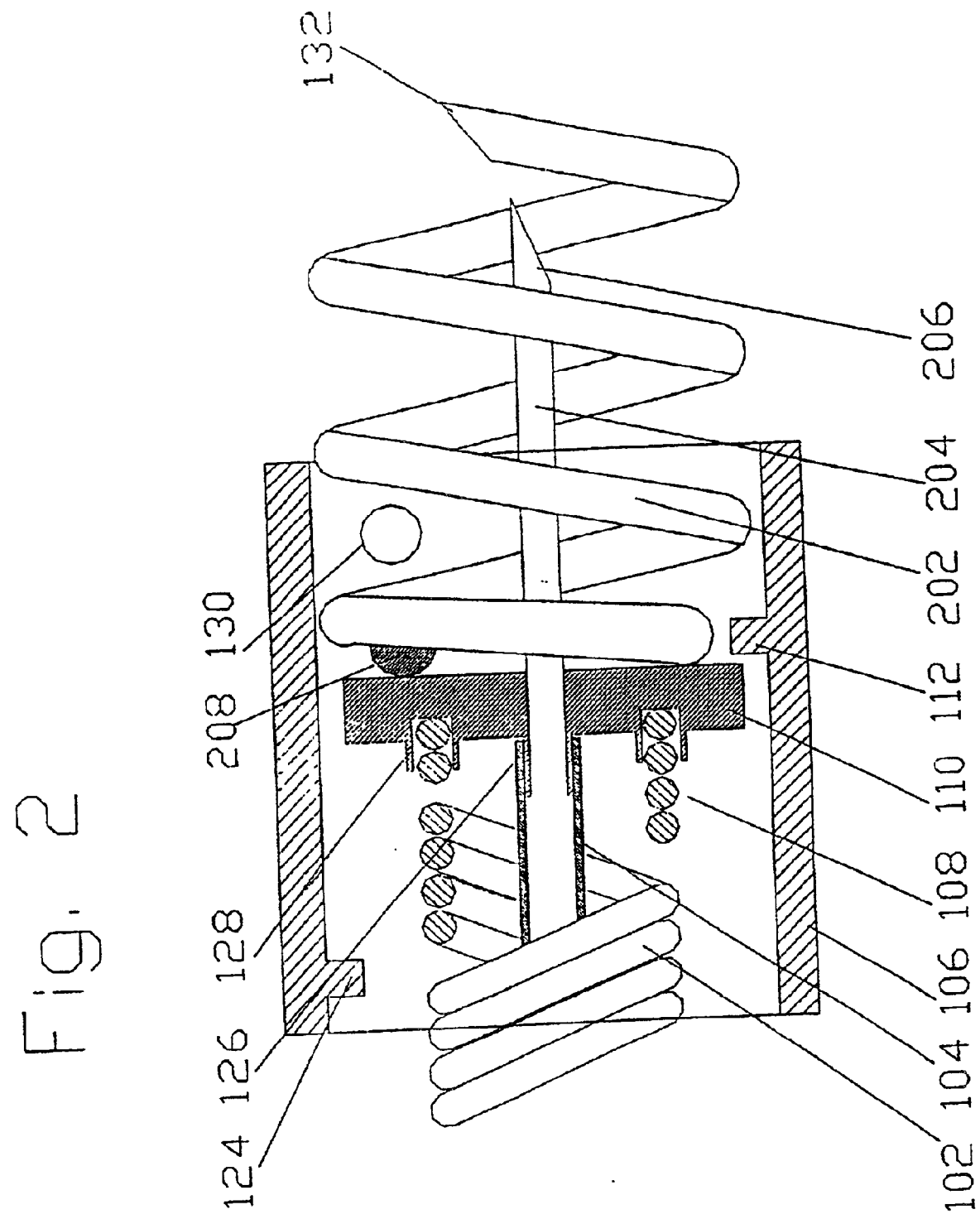
FIG. 2 is a partial cross sectional view of the distal portion of a drug delivery catheter with a short needle located in the axis of the helical fixation device.

New concepts for delivering agents for the treatment of heart failure, ischemia, arrhythmias, and restenosis are disclosed. The main embodiments consist of transvenous or transarterial catheter delivery techniques for delivering agents directly to a chosen site within the heart at a depth within the heart tissue. Hollow helical delivery devices, needle delivery devices, and implantable controlled release matrices may be inserted such that metabolic agents, anti ischemic agents, growth factors, antiarrhythmic agents, anti-inflammatory agents anti-proliferative agents, gene therapy preparations, and combinations of these agents may be delivered directly to the tissue that can benefit most from these agents.

These drug delivery structures may be made from different materials depending upon whether the device is to be used chronically or acutely. For example, metal components in the preferred implantable embodiments, formed of a Platinum Iridium alloy consisting of ninety percent Platinum and ten percent Iridium, typically are replaced with 316L surgical stainless steels in the acute embodiments. Likewise implantable grades of silicone and polyurethane are replaced with polyurethanes, polyolefins, fluoropolymers, nylon, and the like in the acute uses of the devices. Herein the term catheter is used to describe both chronically and acutely implantable systems.

FIG. 1a shows a first cardiac drug delivery catheter with a sectional view of the proximal end. A pin 2 is shown mechanically crimped at a crimp 6 to an electrically conductive helical coil 8. Crimp 6 is typically covered by a compliant polymer molding 4 which may form a seal with a catheter port on a drug delivery reservoir or pumping means 16. Such a reservoir, shown schematically at 16, may be implanted subcutaneously or located outside the patient. A line 18 represents a fluid coupling of reservoir 16 to lumen 12, which enables delivery of fluid treatment agents from the reservoir to fixation end 24. Further molding 4 and a catheter body or sheath 14 may have external sealing rings to provide fluid tight seals with such ports. Pin 2 connects to an internal tubing 10 with a lumen 12 which extends the entire length of the catheter to the distal end 22 and allows for fluid agents to be delivered through a fluid pathway in a fixation end 24. The catheter body or sheath 14, 20, and 22 covers the coil 8 along the entire length of the delivery system distal to crimp 4 such that rotation of pin 2 or crimp 4 relative to proximal catheter body 14 rotates coil 8 within catheter body 14, 20, and 22 and deploys fixation mechanisms at fixation end 24. The central lumen 12 in some embodiments may also be used to pass a stylet for use during implantation to facilitate the implantation procedure.

The catheter shown in FIG. 1a is made of permanently implantable materials, it has electrical continuity from end to end for sensing cardiac activity, it has a lumen for conveying fluidic agents along its length, and a hollow fixation means for delivering fluidic agents to a depth within the heart tissue.

Further as to the sensing of cardiac activity, a monitor and control device 26 is electrically coupled to pin 2 through a line 28, thus to enable a sensing of highly localized cardiac electrical activity at device 26. Cardiac activity can be recorded at device 26, e.g. stored in a memory chip (not shown). Further, sensed cardiac activity may be employed to provide controlling signals to reservoir 16 through a line 30, e.g. to initiate or terminate the supplying of a fluid agent from the reservoir, responsive to sensing a predetermined activity or condition in cardiac tissue proximate fixation end 24. The materials selected are suited for permanent implantation to provide for transient drug delivery driven by a proximal reservoir and energy source. For example, catheter body 14, 20, and 22 is an implant grade polyurethane or silicone, and the distal fixation mechanism at fixation end 24 is a platinum iridium alloy. The catheter has a single electrode to facilitate implantation by sensing the electrical potential at the implant site. This combination achieves the advantages of ease of implantation, and delivery of fluidic agents to a depth within the heart from a proximally located reservoir.

In another embodiment, the monitor and control device 26 is not required. Instead, reservoir 16 pumps at a low, constant rate, supplying infusing agents to a depth within the myocardium, thus to locally apply selected agents, such as angiogenic growth factors, at a steady rate over an extended period, e.g. one week.

FIG. 1b shows another embodiment of the proximal end of a catheter delivery system in which a stylet lumen 66 is provided for insertion of a stylet. Such an additional lumen may be useful to prevent contamination of an inner drug delivery tubing 62 during implantation. Inner tubing 62 is connected to a pin 52 at a connection 56, which may be performed simply by pulling tubing 62 over pin 52 at connection 56. An electrically conductive coil 60 surrounds tubing 62 and may be rotated relative to outer jacket or catheter body 58 of the delivery system. After implantation using a stylet in stylet lumen 66, pharmacological agents may be delivered to the heart by a fluid pathway defined by a delivery system lumen 64. In this specific embodiment, crimp 54 which connects pin 52 and coil 60 is not overmolded, and a single set of seals 70 are shown molded over the proximal end of catheter body 58. Seals 70 prevent migration of fluids into the catheter after connection with a catheter port in a drug delivery reservoir or pumping means. In one embodiment, the distal end of the drug delivery catheter shown in FIG. 1b would be the distal embodiment shown in FIG. 5b.

FIG. 1c shows a partial cross sectional view of the distal portion of a delivery catheter which is to be implanted endocardially by the appropriate venous or arterial access. Here, a simple pathway for fluid to pass from a subcutaneous reservoir or delivery pump (not shown) through a deployable helical needle is provided. Helical coil 102 is multifilar, but could be single filar as well. The number of filars can be varied to determine the flexibility of the catheter as well as the coil's ability to transmit torque to fixation helix 114. The fixation helix is screwed into the heart by turning a coil 102 inside an outer catheter body 106. A fixed structure 130, on the inner wall of the catheter body 106, facilitates advancement and retraction of the fixation helix 114 by forcing the helical fixation structure 114 to advance from the distal end of the catheter when the central helical coil 102 and tube for drug delivery 104 are rotated counterclockwise. Fixed structure 130 is typically formed from a radio opaque material to assist the implanting physician in identifying when fixation helix 114 has been deployed. Fixed structure 130 also will retract the fixation helix 114 from the heart wall when the coil 102 is rotated clockwise. These directions could be reversed by varying the direction of the winding of the fixation helix 114. The helical coil 102 which provides torque to implant the fixation helix 114 is welded or crimped to a coupling structure or torque delivery structure 110 at a coil to torque delivery structure connection 128. Here, the coil is shown crimped at connection 128. Proximal stop 124, and distal stop 112 are raised portions on the inside of the catheter body 106, and prevent the fixation helix 114 from being extended or retracted too far. A fluid path is provided from the proximal end of the catheter (not shown) by tube for drug delivery 104 which connects to the tube fitting 126 of the hollow fixation helix 114. The hollow fixation 114 may have a number of small holes or helix apertures 116, 118, 120, 122 along its length where it is penetrated into the heart tissue. These holes provide a means for delivering agents into the heart tissue at a depth within the tissue. Helix tip 132 is sharp to facilitate penetration of the heart tissue, and acts as a further opening for the agents to migrate from the tissue. In some embodiments the helix apertures may be on only the distal portion of the helix to minimize the possibility of agents being delivered within the heart chambers. In other embodiments, the helix apertures are not present to maximize the structural integrity of the fixation helix. Where this is the case, agents are delivered to the heart from the aperture at the hollow helix tip 132. The fixation helix 114 is rigidly attached to the torque delivery structure 110 to provide means for advancement when coil 102 is rotated.

FIG. 1c shows a means for delivering agents by a fluid path to a depth within the heart tissue, to provide a wide variety of agents by way of a fluid pathway to a depth within the tissue from a proximally located reservoir. Helix 114 acts as an electrode, with electrical energy being transmitted along helical coil 102 to and from fixation helix 114 by way of electrically conductive torque delivery structure 110. It can be viewed as the distal end of the implantable catheter whose proximal end is shown in FIG. 1a or FIG. 1b. In one embodiment, the device of FIG. 1 could be used for chronic delivery of antiarrhythmic agents to alter local conduction either continuously, or on demand based upon the signals sensed through fixation helix 114. Such algorithms have been described for pharmacological atrial defibrillation by Arzbaecher in U.S. Pat. No. 5,527,344. In other embodiments agents for a variety of disease states may be continuously infused by the fluid pathway to a specific site within the myocardium. The proximal end of the catheter may be connected to a drug pumping mechanism or to a proximally located reservoir. Such proximal devices may be implanted or located outside the patient. Access to implantable proximal devices for refilling agents is achieved with a subcutaneous port.

Transient delivery of pharmacological agents based upon demand requires the presence of electrical conductors along the length of the drug delivery catheter to monitor the electrical action of the heart, e.g. the heart rate as indicated by a time-dependent voltage. Delivering of agents upon demand locally alters the conduction or automaticity of the cardiac tissue and allows for the arrhythmia to be treated. Only a small amount of drug is required to treat a specific location within the tissue, which has substantial benefits. Small doses of antiarrhythmic agents minimize the need to refill the proximally located reservoir; and reduce the systemic effects from large drug doses as well as the effects of the agents on normally functioning cardiac tissue. In one application of this embodiment, the device is implanted in the right atrium at a location determined to be most likely to terminate a patients supraventricular arrhythmia. A subcutaneous infusion pump is triggered by the electrical activity of the heart, and a very small region of tissue receives local drug delivery for a preprogrammed duration. A small region of heart is then modified such that cardiac excitation wavefronts are altered by the tissue treated. This provides substantial advantages to patients. Typical of the drugs delivered are antiarrhythmic agents such as those described in U.S. Pat. No. 5,551,427 issued to Altman.

In another embodiment, the device in FIG. 1c is an acute catheter made of nonimplantable materials. Catheter body 106 is formed of polyurethane or a fluoropolymer such as ETFE or PTFE; helical fixation structure 114, and torque delivery structure 110 are made of Titanium or 316L stainless steel. Such a catheter is used for acute ablation procedures in which antiarrhythmic agents are delivered to temporarily alter the conduction of the heart at the site of the implanted helix. Electrical mapping and stimulation measurements are made to determine if the region is appropriate to be ablated. If the region is not appropriate the device is removed and repositioned. If the region treated by the antiarrhythmic agents which affect tissue conduction is desired to be ablated, RF energy is delivered from the electrically active helix to a large surface electrode, such as that used in electrocautery. Such an electrode is shown schematically in FIG. 1a as a patch electrode 32 that can be in contact with the patient's skin outside the body. A conductor 34 electrically couples electrode 32 with monitor and control device 26, whereby device 26 is employed in a known manner to utilize a circuit including conductors 28 and 34, electrode 32, pin 2, crimp 6, coil 8 and a fixation element at the distal end of the coil, to generate an RF current through tissue between the fixation element and electrode 32. The region ablated is that near the surface of the implanted helix. The helical coil 102 is highly conductive to enable RF energy to be conducted to the distal fixation structure to allow ablation of the region immediately at the fixation structure. Such a high conductivity coil can be formed from a number of wires wrapped in parallel in which each wire has a high conductivity silver core jacketed by an MP35N non corrosive alloy. This catheter provides for both temporary modification of tissue conductivity by delivery of therapeutic agents to a depth within the tissue, and delivery of RF energy from the same structure.

FIG. 2 shows another distal portion of a delivery catheter for endocardial placement. The operation is similar to that just described. However, here the fixation structure 202 is solid and does not provide a fluid path for delivery of agents. The fluid pathway is instead provided by a centrally located hollow needle 204. Apertures could also be made along the needle to provide more exposure to the tissue within the heart wall. Fluid agents flow through connecting tube 104, inside the hollow needle 204, and out through apertures in the surface (not shown) and the needle tip 206. Agents are delivered via the needle to a depth within the tissue. Thus, needle 204 provides a tissue penetrating element distinct from the fixation element, whereas in FIG. 1c the penetrating element and fixation element are the same, i.e. helix 114. The solid fixation structure 202 advances in the same manner as described in FIG. 1, and may be rigidly attached to the torque delivery structure 110 by a weld 208. Other methods of connection are possible. The primary advantage of this design is that the solid helical fixation structure 202 is structurally more robust than that of the hollow structure shown in FIG. 1c. This facilitates implantation of the structure.

Other embodiments which incorporate osmotic pumps, controlled release matrices, membrane barriers, and catheter based transient delivery means increase the ability to control the delivery of agents to a depth within the heart tissue. They have substantial advantages in delivering agents such as growth factors and gene therapy preparations in that very small amounts of the agents are effective, the delivery is controlled over time, and the agents are delivered to a depth within the heart.

Figure 3K:
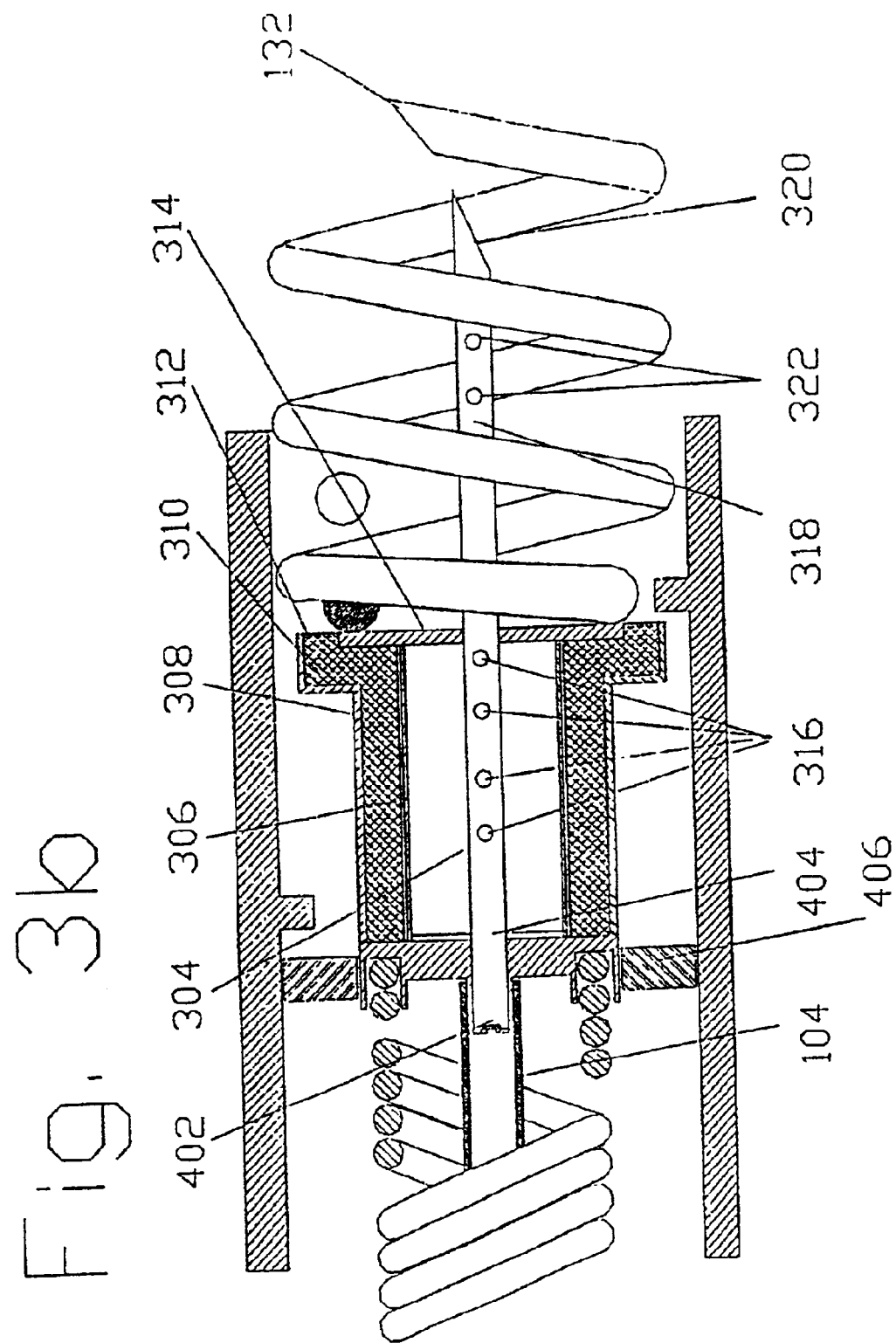
FIG. 3a is a partial cross sectional view of the distal portion of a drug delivery catheter which incorporates an osmotic pump.
FIG. 3b is a partial cross sectional view of the distal portion of a drug delivery catheter which incorporates an osmotic pump.

FIG. 3a shows an osmotic pump located at distal end of a catheter to drive therapeutic agent into heart tissue using a needle 318. Alternatively a hollow helix fluid transport system as described can be employed. Agents may be delivered via the fluid pathway previously described, through the check valve 302, and into the drug volume or drug reservoir 304. After the drug reservoir 304 is full, agents migrate out the needle tip 320, and apertures 322. Reservoir 304 may be loaded before, during, or after implantation from the proximal end of the drug delivery catheter. Once advanced into the heart tissue, diffusion of a liquid across the semipermeable membrane 312 occurs because of an osmotic salt 310. As this salt expands with hydration, pressure is exerted against the flexible barrier 306 and the rigid osmotic pump housing 308. The expansion constricts the drug volume 304. As check valve 302 is closed to reverse flow, the agents are forced through the delivery structure and into the heart wall. The pathway to needle tip 320 includes proximal needle apertures 316 and proximal needle opening 324 within the reservoir 304. The rigid support 314 supports the fixation helix and the needle delivery structure.

Placing an osmotic pump directly at the site where agents are delivered has the benefit of limiting the amount of agent in the system. In devices where the agent in the filling tube can be removed, the site specific osmotic pump does not require a long length of tubing filled with pharmacological agent. This may be particularly useful for agents whose systemic effects are undesirable or unknown. To deliver agents by a fluid pathway along the length of a catheter system requires a length of tubing to be filled with the appropriate agent. Although minimizing the cross sectional area of such a tube reduces excessive amounts of agents, putting the pump at the site for delivery eliminates the problem. Placing the osmotic device at the end of the catheter tube provides the advantageous means for follow-up delivery after the pump has delivered all of the agents in the reservoir 304. Further, only a very small amount of agent is required and the osmotic pump is placed on a catheter at the site for delivery. A catheter based osmotic pump as in FIG. 3a may be filled proximally after implant, and agents may be altered during delivery. Such delivery techniques have substantial advantages for macromolecules such as growth factors and genetic material. Further, they may allow for very controlled delivery of microsphere or micelle encapsulated agents.

The drug reservoir 304 can contain either a solution or a solid formulation in a semipermeable housing with controlled water permeability. The drug is activated to release in solution form at a constant rate through a special delivery orifice (e.g. either 316 or 322). The release of drug molecules or encapsulated drug molecules from this type of controlled release drug delivery system is caused by osmotic pressure and controlled at a rate determined by the water permeability and the effective surface area of the semipermeable housing as well as the osmotic pressure gradient. Devices which use hydrodynamic pressure gradients are similar except the semipermeable membrane is replaced by an opening, and the osmotic salt is replaced by an absorbent and swellable hydrophilic laminate.

FIG. 3b shows a partially sectional view of another embodiment of the distally located osmotic pump. Here a check valve 402 is located at the proximal end of a needle 404 which extends through drug volume or reservoir 304. Needle 404 provides more structural stability to the drug delivery device and guarantees a fluid pathway to the delivery needle 320 even after the osmotic action has driven all of the agent out of the drug volume 304. Further, a section of a seal 406 is shown attached to the inside of the catheter body. Osmotic pump housing 308 is moveably contained within seal 406, which acts to prevent migration of fluids into the catheter body.

FIG. 4 shows another embodiment of a cardiac drug delivery system. Here the fixation mechanism consists of a needle 484 with apertures 486 that penetrates the myocardium and is held in place by barbs 466. In a chronic implant barb 466 may be composed of either a rigid metallic alloy or a biodegradable polymer. If a biodegradable material is used, long term tissue attachments will maintain fixation with the heart, and the barb 466 will not cause undue trauma should the drug delivery system need to be explanted.

In addition, FIG. 4 shows a multilumen catheter and valve system for the filling of reservoir 462. Agents are delivered along the fluid path defined by a filling lumen 452 in a bitumen tubing 450 such that unidirectional check valve 456, shown here as a ball check valve, is opened allowing agents to flow through lumen 458 of tube 460 and out the distal end of tube 480. The ball check valve has a sphere in a generally conical tube which allows unidirectional flow by obstructing the smaller diameter fluid pathway to reverse flow and not obstructing the larger diameter circular pathway of the open flow direction in various embodiments it could be replaced with a reed check valve, a hinged plate check valve, or the equivalent. After the reservoir 462 is filled, the fluid will open check valve 472 and flow out clearing lumen 468 in bilumen tube 450. This filling action will force ball check valve 470 closed. After filling, the remaining agent in the bilumen tube may be cleared by delivering sterile distilled water, which may contain anticoagulants such as heparin to assure long term patentcy of the catheter lumens, to clearing lumen 468. This clearing fluid will force check valve 472 closed, and check valve 470 open such that agents may be flushed from the bilumen tube and replaced with the distilled water or other flushing agents. If the system is chronically implanted, such a bilumen tube and series of valves would allow one to fill the reservoir 462 and clear the bilumen tube 450 after implant. Further, because the distal end of the tube 480 allows for filling of the reservoir 462 from the distal end, agents may be changed merely by filling via filling lumen 452 which will force the existing agents out through proximal reservoir exit 474, through valve 472 and clearing lumen 468. If the proximal end of such a bilumen delivery system were connected to a dual port subcutaneous reservoir (not shown) agents would be injected into one port while withdrawn from the second port.

In this delivery catheter, the distal housing also acts as an osmotic delivery system with semi permeable membrane 496, hydrophilic salt or agent 476, and flexible polymer barrier 464 allowing for controlled delivery of agents over a period of time. After the expiration of the osmotic energy source, agents may be delivered via the fluid pathway by an external pumping means if desired. The valve housing 454 houses the three unidirectional valves 456, 470, and 472, and provides tube fittings 488 and 490 for connection to the bilumen tubing. This valve housing 454 is also attached by a crimp 494 to the coil 492. This structure is assembled from the separate components and combined. Alternatively, separate valves could be fit into openings in a simpler metallic form, and the whole mechanically and hermetically attached to the rigid osmotic pump housing 478. Rigid support 482 is fixed to needle 484, and may also have structural elements which enter into the region of the hydrophilic salt, and possibly attach to the valve housing 454.

Figure 5A:
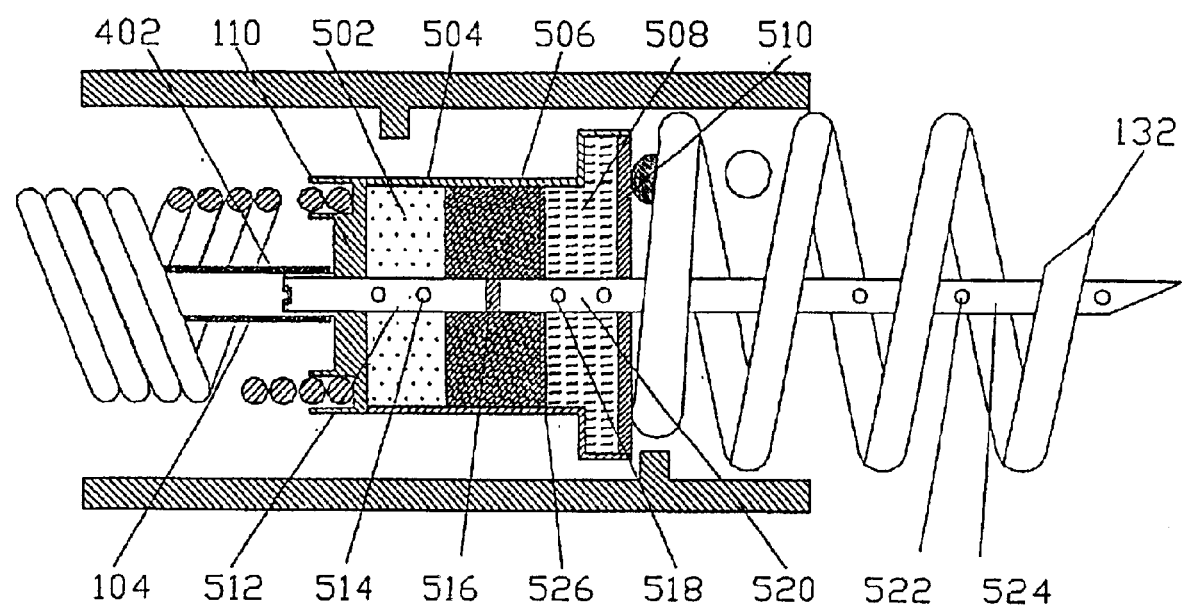
FIG. 5a is a partial sectional view of the distal portion of a drug delivery catheter with a rate control barrier.

FIG. 5*a* shows partially in section an embodiment where a membrane or rate controlling barrier 506 stands between the agent reservoir 502 and the apertures 518 in the proximal end of the delivery needle 520 which would allow the agents to be delivered to the distal end of the delivery needle 524, and through the apertures 522. The needle could be replaced with a hollow helical delivery device as shown in FIG. 1*c* if desired. An optional controlled release structure 508 provides chronic delivery of agents to the implant site. As this agent diminishes, new agents can be provided through the connecting tube and check valve 402, such that rate of release is governed by control barrier 506. Barrier 506 is shown here with substantial thickness, but it could be formed of a simple membrane, a membrane reinforced with a substantially porous structure, such as a laminate of expanded polytetrafluoroethylene (ePTFE), or any other structure which could be used to govern the rate of drug delivery to the side of the barrier connected by a fluid pathway to the tissue to be treated. The design of the control release barrier would be customized for the agents to be delivered and may be intentionally designed to specify a rate of delivery substantially different from that which the optional control release structure 508. Needle plug 516 prevents flow through the needle lumen, while maintaining a rigid axial support, and could be formed of an inert polymer or metallic material. Rigid support 510 acts to support axial location of needle 524 and may be a mechanical base for the helical fixation means. Controlled release structure 508 could be composed of a macromolecular controlled release matrix such as EVAC housing a growth factor such as TAF, bFGF, or aFGF.

In another preferred embodiment of FIG. 5*a*, controlled release structure 508 would be left out and the space would be filled with pharmacological agents and act as a reservoir for acute delivery immediately after implantation. The fluid path for subsequent agents would then include tubing 104, check valve 402, proximal needle 512 and proximal apertures 514 into agent reservoir 502, contained by drug reservoir housing 504. The fluid agent then passes through rate control barrier 506 acute into the fluid reservoir.

In other embodiments of FIG. 5*a*, the control barrier 506 could be electrically activated to allow rapid delivery of positive pressure and agent delivery from one side to the other. In this electrically activated embodiment, the optional control release structure or acute reservoir 508 could merely deliver agents acutely to preserve the viability of the fluid pathway for the time when therapy is deemed necessary. Acute delivery of antithrombolytics and anti-inflammatory agents would limit blockages and tissue inflammation resulting from the implantation of the structure in the heart wall and improve the ability of a transient system to deliver agents quickly and effectively to the region within the tissue. An electrically controlled barrier could be fashioned much like any electrically controlled microvalve.

Figure 5B:
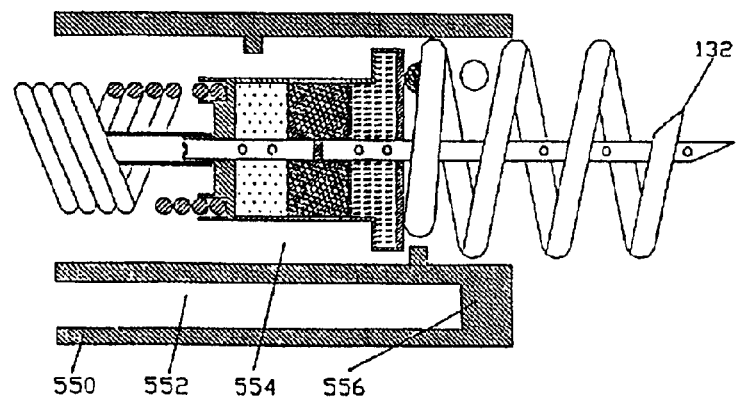
FIG. 5b shows a partially sectioned view of the distal portion of a drug delivery catheter with a second lumen for stylet use during implantation.
Figure 5C:
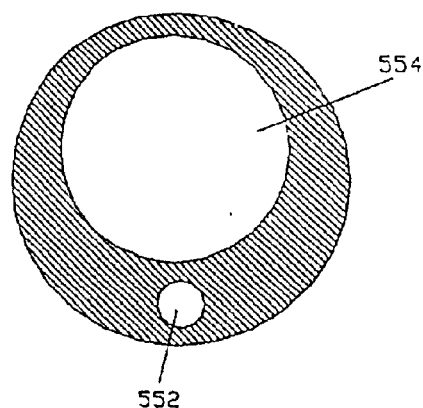
FIG. 5c is a transverse section of the catheter in FIG. 5b.

FIG. 5*b* is a partially sectional view of the drug delivery system described in FIG. 5*a* which incorporates a separate stylet lumen 552 within the same catheter body 550. Such a stylet lumen accommodates a removable wire element to allow the implanting physician to control the shape of the device to guide it to the appropriate site. This additional lumen 552 allows the drug delivery tubing to travel the length of the coil in its own lumen 554. Although shown here as a continuous part of catheter body 550, stylet end stop 556 usually is attached as a separate component. FIG. 5*c* shows the diameter of stylet lumen 552 to be substantially smaller than lumen 554. These lumens may change depending upon the requirements for different applications. Such an additional lumen for stylet use could easily be combined with any of the drug delivery systems presented here. This additional lumen will prevent the lumen of the drug delivery tubing 104 from getting obstructed with body fluids during stylet use, prevent damage to tubing 104 by the stylet, and allow the materials of both stylet and tubing 104 to be chosen without regard to the requirements of the other.

Figure 6:
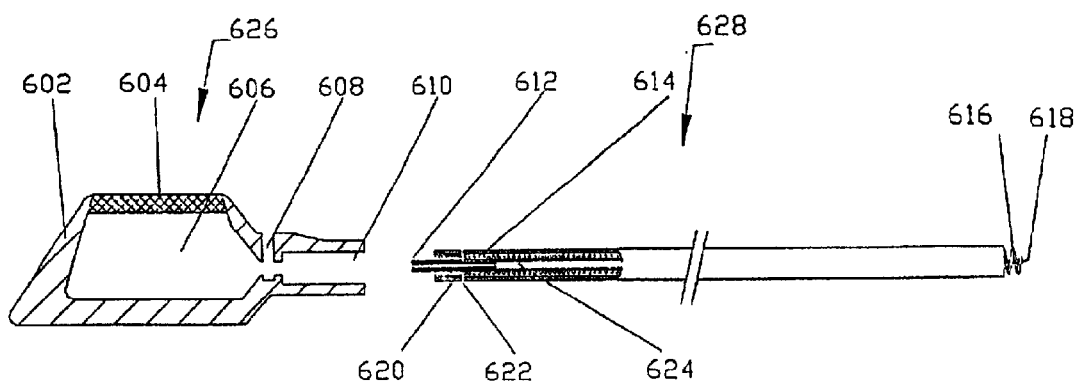
FIG. 6 is a partial sectional view of a subcutaneous injection port, and a drug delivery catheter.

FIG. 6 is a partially sectioned view of one preferred embodiment of a subcutaneous reservoir structure 626 and a drug delivery catheter 628. Subcutaneous reservoir structure 626 may be connected to the proximal end of the delivery catheters shown. Subcutaneous reservoir structure 626 consists of a housing 602 whose reservoir 606 may be filled with a fluid pharmacological agent. The agent is introduced by transcutaneous injection into the reservoir 606 through the polymer injection barrier 604. This barrier is typically composed of silicone rubber such that it creates a seal after removal of the filling needle. In addition, the housing 602 is typically constructed of titanium, polyurethane, or other known rigid biocompatible and nonreactive materials.

FIG. 6 shows a means for connecting the drug delivery catheter to the subcutaneous reservoir, a constant pressure pumping means, or automatic infusion pump. Subcutaneous reservoir structure 626 has a port 610 which accepts the proximal end of delivery catheter 628 such that the region of separation 622 between the crimp structure 620 and proximal end of the jacket body 614 is completely within port 610. This prevents fluids from entering the separation 622 which allows the coil and inner tubing 624 to rotate relative to the jacket body 614 for advancement of fixation structure 616 and needle delivery system 618. After the proximal end is inserted into port 610 of subcutaneous reservoir structure 626, a set screw may be advanced within threads 608 to secure the catheter in position by applying force to pin 612. This set screw connection to the pin is common in devices used to deliver electrical therapy to the heart, and could be used to perform an electrical connection to the fixation means 616 or needle 618 in order to sense the electrical activity of the tissue. This electrical signal could be monitored by devices with algorithms similar to those designed to deliver electrical therapy to the heart, accept that instead of electrical therapy they introduce pharmacologic therapy.

Figure 7:
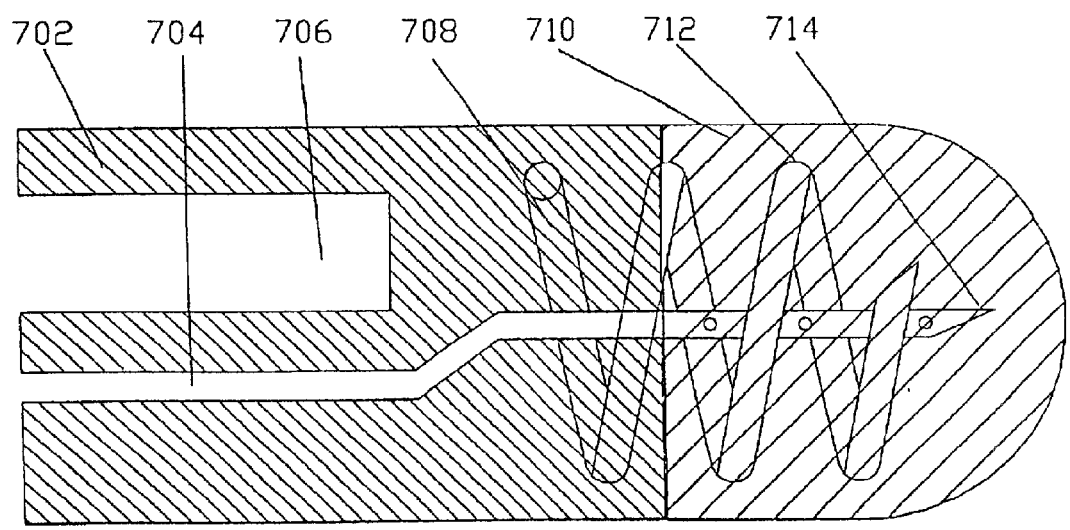
FIG. 7 is a partial sectional view of the distal end of a drug delivery catheter.

FIG. 7 shows another embodiment of an acute drug delivery system. The catheter body 702 houses a lumen 704 for fluid transport of therapeutic agents and a lumen 706 for stylet use during implantation. Lumen 704 travels the length of the delivery catheter and connects to needle delivery structure 714. During implantation through the vasculature, blood soluble coating 710, e.g. as in U.S. Pat. No. 4,827,940 issued to Mayer, completely protects the vasculature from the sharp elements of the fixation helix 712 and the needle delivery structure 714. Blood soluble coatings such as sugars may be used. After the appropriate heart chamber is accessed, the physician waits for the coating 710 to dissolve. The coating may be combined with a radio opaque material such as barium sulfate to identify better when this has been accomplished. After the coating 710 has dissolved, the physician implants the fixation helix 712 by rotating the entire catheter about its own axis. Torque is delivered from the catheter body 702 to the fixation helix 712 by the embedded portion 708 of the fixation helix. This embedded region can be manufactured using molding and bonding technology. The principle advantage of this device is the small cost of manufacturing such a simple design with no moving parts.

Figure 8A:
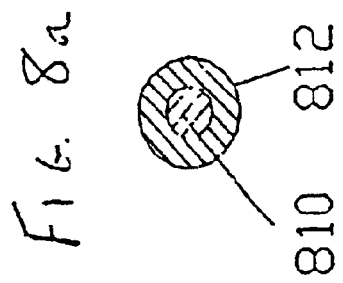
FIG. 8a is a transverse section of the fixation means in FIG. 8.
Figure 8:
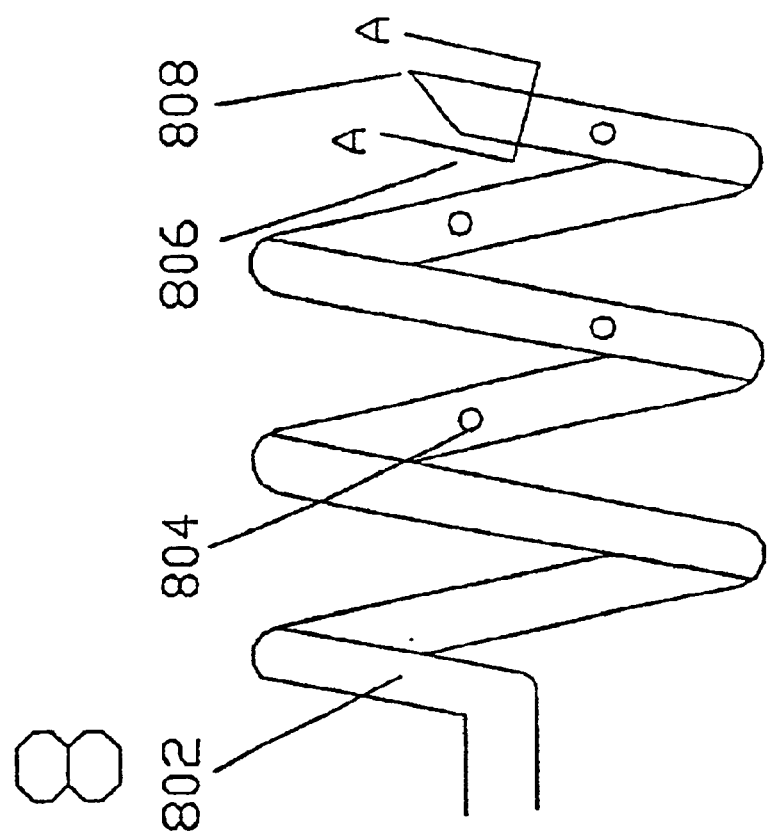
FIG. 8 is a partial sectional view of a filled helical drug delivery fixation means.

FIG. 8 shows a hollow fixation helix 802 with apertures 804 along its length. FIG. 8a shows the hollow helix to be filled with a second material 810. Second material 810 in the preferred embodiment is a controlled release polymer matrix filled with a therapeutic agent for extended delivery of agents through apertures 804 in fixation helix 802. In one embodiment the controlled release matrix is comprised of silicone rubber and the agent to be delivered is lidocaine. In another embodiment the agent may be amiodorone HCL. In another embodiment, the controlled release matrix is EVAC and the agent is aFGF. Other variations are also possible. After implantation of the structure within the heart wall by penetration of helix tip 808, the rest of the helix is rotated such that all apertures 804 are within the tissue. Agents then migrate from the controlled release matrix to the tissue in which it is implanted. Such a controlled release matrix filling of the hollow core which penetrates the heart could be pursued with other penetrating structures as well.

Figure 9:
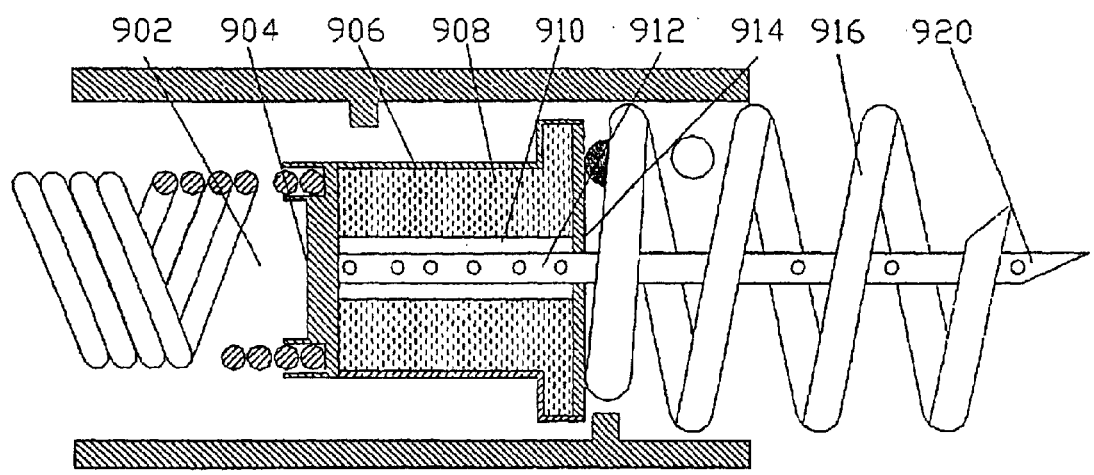
FIG. 9 is a partial sectioned view of the distal end of a drug delivery catheter.

FIG. 9 shows a drug delivery system with VEGF in an EVAC matrix 908 housed in a reservoir defined by cylinder 906, and ends 904 and 914. In the preferred embodiment, these are nonpermeable, although in other embodiments permeability may be desirable. End 904 acts both to transmit torque to fixation helix 916, but also as a stop for a stylet (not shown) which may be used during implantation down the coil lumen 902. After implantation of the drug delivery catheter, body fluids migrate through apertures in distal needle 920 and into a reservoir through a proximal region 912 of the needle and dissolve pharmacological agents in acute dosage 910 which may be present to counter inflammation associated with implantation. Over time, growth factors are delivered via needle 920 to a depth within the heart. Note that the absence of a tube for agent delivery enables stylet use during implantation. In variations on this embodiment, other controlled release means could be housed within a semi permeable structure that would allow increased fluid transport to assist in delivery of agents through needle 920 to a depth within the heart wall.

Figure 10A:
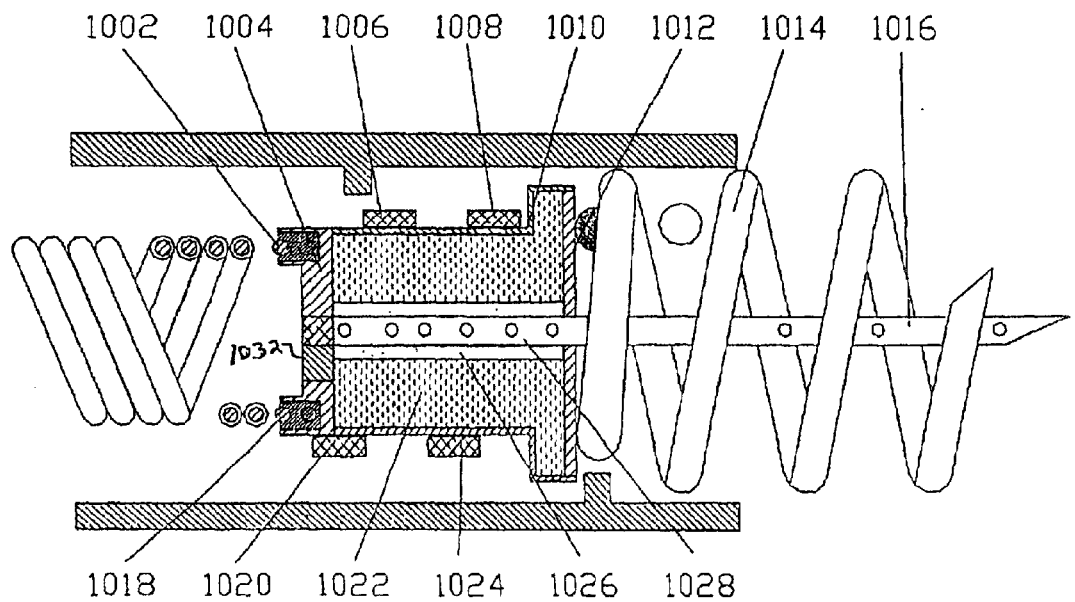
FIG. 10a is a partial sectioned view of a drug delivery catheter with a nitinol transient delivery means.

FIG. 10a shows another drug delivery catheter in which agents may be delivered transiently to a depth within the tissue. Here, helical coil consists of four coradial wires which are electrically isolated from one another by a layer of insulation. The electrical insulation allows a current pathway to be defined which allows current to flow through electrical connection 1018 from two of the coradial wires and into Nitinol thermally activated shape memory ribbon or band 1020, which wraps around flexible polymer barrier 1010 as shown in section. Current flowing through Nitinol ribbon 1020 completes its circuit to the other two coradial wires at electrical connection 1002 to torque delivery structure 1004 via conduction through a connection to support structure 1012 which is electrically connected to needle 1028. Insulating structure 1032 separates the two electrical connection regions on torque delivery structure 1004 and allows current to pass through ribbon 1020. If the electrical resistance of the Nitinol is sufficiently high, ohmic heating causes a constricting shape change upon the flexible polymer barrier 1010. Contained within flexible polymer barrier 1010 is a partially porous polymer controlled release matrix structure 1022 such as silicone rubber containing lidocaine, which upon compression by the Nitinol ribbon, forces agents out of the controlled release matrix 1022 and into the needle 1028 within the reservoir 1026, then out the distal region 1016 of the needle into the heart.

FIG. 10b shows another transient drug delivery structure in which a reservoir contains a fluid whose vapor pressure provides the energy to delivery therapeutic agents. As in FIG. 10a, the different filars in the helical coil, such as filar 1068, are electrically insulated from one another such that two independent electrical connections may be made at a crimp 1050 and a crimp 1072 which are separated from each other by electrically insulating barrier 1070. The electrical connections made at crimp 1050 and 1072 have an electrical path between them which is defined by resistive heating element 1052 which passes through a reservoir 1056. Within reservoir 1056 is a fluid gas mixture which provides a constant pressure at human body temperature via a plate 1058 to a drug matrix 1060. If drug matrix 1060 is a substantially porous controlled release matrix, the pores surrounding the matrix will be filled with relatively high concentration of agents in fluids. As electrical energy is delivered along the two independent electrical conductors to resistive heating element 1052, the temperature of the fluid within reservoir 1056 increases. As reservoir housing 1066 and support structure 1064 are rigid and noncompliant, this increases the pressure within reservoir 1056 to cause expansion of bellows 1054 and apply pressure to the controlled release matrix 1060. This forces the concentrated fluid from within the porous controlled release matrix into proximal end of needle delivery system 1074 and out through the distal end of the needle into the heart wall. Such vapor pressure energy sources have been used in infusion pumps such as an infusion pump available from Infusaid of Norwood, Mass. However, that system has not been implanted on a catheter, nor does that pressure system provide a thermal element to increase the temperature within the charging fluid and thus deliver the pressure transiently. In addition to the porous matrix, there is a soluble anti-thrombogenic and anti inflammatory agent for use in acute dosage form 1062 which surrounds proximal length of needle 1074, while still leaving the end free for agent administration. Such acute dosage forms may be very useful for guaranteeing the long term outcome of such controlled delivery systems by minimizing the response of the tissue to the trauma of implantation.

A method for delivering therapy using a combined drug delivery ablation catheter proceeds as follows. Initially the arrhythmogenic site is located using techniques common to those in the field of cardiac electrophysiology. The delivery system is inserted into the appropriate site within the heart by the internal or external jugulars, cephalic vein, subclavian vein, femoral artery, or the other vascular delivery routes. Then, the drug delivery structure is implanted at the arrhythmogenic site supply an appropriate agent for altering the local conduction properties. After implantation, agents are delivered and the effect on the arrhythmogenic site is evaluated by electrical techniques such as mapping. If the location is appropriate, and the agents appear to terminate the critical arrhythmia, RF energy is delivered to the tissue by way of the same structure used to deliver the agents to the heart. If the position is inappropriate and the local pharmacological agents do not correct for the arrhythmia, the device is repositioned, and the procedure repeated.

A method for transient treatment of supraventricular arrhythmias using a chronically implantable transient drug delivery catheter proceeds as follows. After electrophysiologists have specified the appropriate region for implantation based upon the patient's cardiac electrical action, a catheter is implanted at this site to deliver antiarrhythmic agents at a depth within the heart transiently, as well as to sense the electrical activity near the device. The catheter is then connected to an external controller and power source, which determines suitability of therapy and delivers energy to a device such as those described in FIGS. 10a and 10b for transient delivery of pharmacological agents, or to a device such as that shown in FIG. 1c coupled to a proximally located pumping means. The device then senses cardiac activity through the surface of the drug delivery structure. When the heart experiences an arrhythmic event, the controller identifies the event and activates the energy source which delivers the drug to the heart. This drug modifies the selected area of tissue and either terminates the arrhythmia, or substantially reduces the magnitude of the required electrical therapy. If the arrhythmia does not terminate, the pump may deliver a secondary dosage, or trigger an external electrical therapy device. If no arrhythmia is sensed, the device is maintained in a monitoring mode.

Thus the different embodiments of the invention provide a means to effectively deliver agents at a depth within the myocardium to provide a new means for delivering pharmacological therapy to specific locations within the heart. These delivery systems will allow therapies for ischemic tissue, arrhythmogenic sites, and other cardiac disease to be delivered over an extended period of time through a chronic implant, or rapidly over a short period of time during an acute procedure. They enable controlled delivery of small amounts of macromolecular agents such as growth factors, transient drug delivery to the tissue for treating cardiac arrhythmias, and may be used with other cardiac devices.

Many other variations are possible. For example, the flow of liquid agents maybe driven by implantable infusion pumps with a variety of energy sources, and the device could be made from different biocompatible materials. Other examples include distally located electrically activated piezoelectric crystals as energy sources for drug delivery, and distally located ultrasound transducers for implantation using ultrasound imaging. In addition, in the embodiments where unipolar sensing through the drug delivery structure is insufficient, it is a simple task to add another electrode to enable bipolar sensing.

Catheters with a straight cylindrical lumen from one end to the other could be used with a thin bundle of optical fibers passed through the lumen to photoablatively create channels within the heart for improving the flow of pharmacological agents within the heart. In other variations, the thin optical fiber could be replaced with a thin RF electrode structure which could literally burn channels within the tissue. Such procedures could be viewed as a combined transmyocardial revascularization (TMR) and drug delivery. For example, after a catheter is implanted and agents are delivered to minimize reflow damage to the heart, simple TMR could be introduced with a centrally placed optical fiber. Subsequent to the TMR, angiogenic growth factors could be introduced.

In other embodiments, the devices described may be used for acute delivery of metabolic agents, and anti-ischemic agents to poorly perfused tissue just prior to introducing reflow. The agents improve the health of the poorly perfused tissue and minimize the amount of reflow injury introduced by the white blood cells. In another embodiment the devices described may be used to deliver specific antiarrhythmic agents over a time course of days to weeks while physicians determine whether an implantable system is appropriate. In a another embodiment, the catheters described may be used to deliver gene therapy at a depth in the diseased myocardium over a period of days to weeks.

Further, the delivery of the agents could be performed with appropriately modified catheter shapes such that curves are located to effect a certain position within the heart. Such curves in a catheter could be molded into place, or held in place by plastic deformation of the helical coil in the region it is desired. Such curved structures may provide improved access to certain regions within the right atrium, left atrium, right ventricle and left ventricle.

Further, the implantable versions of the different catheters could have their fixation mechanisms coated with radioactive agents such as Phosphorous 32 to emit beta radiation for the minimization of tissue growth on the fixation structures. This has particular advantages for catheters meant to be implanted for durations longer than a few days, to be removed after the therapy has been delivered.

Further, acute embodiments of this device could incorporate standard sensor technologies for measuring pH and P 02 within the heart chamber or even within the myocardium, and mapping electrodes could be placed along the distal portion of the catheter body to facilitate implantation relative to measured electrical signals through the myocardium.

Accordingly, the scope of the invention should be determined not by the embodiments illustrated, but by the appended claims and their legal equivalents.

What is claimed is:

1. A system for supplying a therapeutic agent locally to a depth within cardiac tissue, including:
   an elongate, flexible, dielectric and biocompatible catheter body;
   an elongate and flexible electric conductor coextensive with the catheter body;
   a conductive implantable electrode including a distally located penetrating element comprising a substantially linear, distally extending needle adapted to penetrate cardiac tissue to a depth within surrounding cardiac tissue, said electrode further including a fixation element for securing the electrode within the cardiac tissue;
   a conductive coupling structure electrically coupling a proximal portion of the electrode with respect to a distal end of the flexible electric conductor;
   a fluid passage through the electrode, open to an exterior of the electrode at said proximal portion and at said penetrating element;
   a source of a therapeutic agent, fluid coupled to the fluid passage at said proximal portion to deliver a therapeutic agent to said surrounding cardiac tissue via the fluid passage;
   a sensor electrically coupled with respect to a proximal end of the flexible electric conductor for monitoring an electrical condition of said surrounding cardiac tissue; and
   a controller operatively coupled to the sensor and to the source, adapted to control the delivery of the therapeutic agent responsive to the sensed electrical condition.

2. The system of claim 1 wherein:
   said fluid passage is open to the electrode exterior at the penetrating element through a distal end aperture at a distal tip of the penetrating element.

3. The system of claim 2 wherein:
   said fluid passage further is open at the penetrating element through a plurality of apertures disposed along the penetrating element.

4. The system of claim 1 wherein:

said source comprises a reservoir containing the therapeutic agent and a delivery means for effecting delivery of the agent from the reservoir to the fluid passage.

5. The system of claim 4 wherein:

said reservoir is disposed adjacent the proximal portion of the implantable electrode.

6. The system of claim 4 wherein:

said reservoir is disposed near a proximal end of the catheter body, and said source further includes a flexible tubing extending from the proximal end of the catheter body to the distal end thereof, and having an internal lumen fluid-coupled to the fluid passage.

7. The system of claim 6 wherein:

said reservoir is adapted for subcutaneous implantation.

8. The system of claim 1 wherein:

said electrical condition comprises an electrical conduction or a time-dependent voltage.

9. The system of claim 1 wherein:

said flexible electrical conductor is disposed within the catheter body.

10. The system of claim 9 wherein:

said flexible electric conductor is either a helically wound coil or a cable.

11. The system of claim 1 further including:

a surface electrode positionable proximate and in spaced apart relation to said implantable electrode, an electrically conductive path coupling the surface electrode to the controller, and a means acting through the flexible electric conductor to bias the implantable electrode with respect to the surface electrode to generate RF current between the implantable and surface electrodes.

12. The system of claim 1 further including:

a housing disposed near said distal end of the electric conductor and mounted with respect to the proximal portion of the electrode, wherein said source comprises a distal reservoir within said housing, adapted to contain a therapeutic agent and fluid coupled to the fluid passage for delivering the therapeutic agent.

13. The system of claim 12 wherein:

said housing incorporates a component for applying pressure to the therapeutic agent in the distal reservoir to urge the therapeutic agent from the distal reservoir into the fluid passage.

14. The system of claim 13 wherein:

said component comprises one of the following: an osmotic pump, a band formed of a recovery metal surrounding the housing, and a means for applying vapor pressure.

15. A system for supplying a therapeutic agent locally to a depth within cardiac tissue, including:

an elongate, flexible, dielectric and biocompatible catheter body;

an elongate and flexible electric conductor coextensive with the catheter body;

a conductive implantable electrode including a distally located penetrating element adapted to penetrate cardiac tissue to a depth within surrounding cardiac tissue;

a conductive coupling structure electrically coupling a proximal portion of the electrode with respect to a distal end of the flexible electric conductor;

a fluid passage through the electrode, open to an exterior of the electrode at said proximal portion and at said penetrating element;

a source of a therapeutic agent comprising a reservoir containing the therapeutic agent, fluid coupled to the fluid passage at said proximal portion to deliver a therapeutic agent to said surrounding cardiac tissue via the fluid passage, and a delivery means for effecting delivery of the agent from the reservoir to the fluid passage;

a sensor electrically coupled with respect to a proximal end of the flexible electric conductor for monitoring an electrical condition of said surrounding cardiac tissue; and a controller operatively coupled to the sensor and to the source, adapted to control the delivery of the therapeutic agent responsive to the sensed electrical condition;

wherein the reservoir is disposed adjacent the proximal portion of the implantable electrode.

16. The system of claim 15 wherein:

said penetrating element comprises a helical coil, which tends to fix the electrode within the cardiac tissue as it penetrates the tissue.

17. The system of claim 15 wherein:

said penetrating element comprises a substantially linear, distally extending needle, and said electrode further includes a fixation element for securing the electrode within said cardiac tissue.

18. The system of claim 15 wherein:

said fluid passage is open to the electrode exterior at the penetrating element through a distal end aperture at a distal tip of the penetrating element.

19. The system of claim 18 wherein:

said fluid passage further is open at the penetrating element through a plurality of apertures disposed along the penetrating element.

20. The system of claim 15 wherein:

said delivery effecting means comprises a shape memory metal ribbon surrounding the reservoir.

21. The system of claim 15 wherein:

said delivery effecting means employs vapor pressure.

22. The system of claim 15 wherein:

said electrical condition comprises an electrical conduction or a time-dependent voltage.

23. The system of claim 15 wherein:

said flexible electrical conductor is disposed within the catheter body.

24. The system of claim 23 wherein:

said flexible electric conductor is either a helically wound coil or a cable.

25. The system of claim 15 further including:

a surface electrode positionable proximate and in spaced apart relation to said implantable electrode, an electrically conductive path coupling the surface electrode to the controller, and a means acting through the flexible electric conductor to bias the implantable electrode with respect to the surface electrode to generate RF current between the implantable and surface electrodes.

26. A system for supplying a therapeutic agent locally to a depth within cardiac tissue, including:

an elongate, flexible, dielectric and biocompatible catheter body;

an elongate and flexible electric conductor coextensive with the catheter body;

a conductive implantable electrode including a distally located penetrating element adapted to penetrate cardiac tissue to a depth within surrounding cardiac tissue;

a conductive coupling structure electrically coupling a proximal portion of the electrode with respect to a distal end of the flexible electric conductor;

a fluid passage through the electrode, open to an exterior of the electrode at said proximal portion and at said penetrating element;

a source of a therapeutic agent, fluid coupled to the fluid passage at said proximal portion to deliver a therapeutic agent to said surrounding cardiac tissue via the fluid passage;

a sensor electrically coupled with respect to a proximal end of the flexible electric conductor for monitoring an electrical condition of said surrounding cardiac tissue; and a controller operatively coupled to the sensor and to the source, adapted to control the delivery of the therapeutic agent responsive to the sensed electrical condition; and a housing disposed near the distal end of the electric conductor and mounted with respect to the proximal portion of the electrode, wherein the source comprises a distal reservoir within the housing, adapted to contain the therapeutic agent and fluid coupled to the fluid passage for delivering the therapeutic agent.

27. The system of claim 26 wherein:

said housing incorporates a component for applying pressure to the therapeutic agent in the distal reservoir to urge the therapeutic agent from the distal reservoir into the fluid passage.

28. The system of claim 27 wherein:

said component comprises one of the following: an osmotic pump, a band formed of a recovery metal surrounding the housing, and a means for applying vapor pressure.

29. The system of claim 26 wherein:

said penetrating element comprises a helical coil, which tends to fix the electrode within the cardiac tissue as it penetrates the tissue.

30. The system of claim 26 wherein:

said penetrating element comprises a substantially linear, distally extending needle, and said electrode further includes a fixation element for securing the electrode within said cardiac tissue.

31. The system of claim 26 wherein:

said fluid passage is open to the electrode exterior at the penetrating element through a distal end aperture at a distal tip of the penetrating element.

32. The system of claim 31 wherein:

said fluid passage further is open at the penetrating element through a plurality of apertures disposed along the penetrating element.

33. The system of claim 26 wherein:

said electrical condition comprises an electrical conduction or a time-dependent voltage.

34. The system of claim 26 wherein:

said flexible electrical conductor is disposed within the catheter body.

35. The system of claim 34 wherein:

said flexible electric conductor is either a helically wound coil or a cable.

36. The system of claim 26 further including:

a surface electrode positionable proximate and in spaced apart relation to said implantable electrode, an electrically conductive path coupling the surface electrode to the controller, and a means acting through the flexible electric conductor to bias the implantable electrode with respect to the surface electrode to generate RF current between the implantable and surface electrodes.

* * * * *